(12) United States Patent
Wahle et al.

(10) Patent No.: US 6,242,220 B1
(45) Date of Patent: Jun. 5, 2001

(54) METHOD FOR PURIFYING COVALENTLY CLOSED CIRCULAR DNA

(75) Inventors: Stephan Wahle, Köln; Jaochim Schorr, Hilden; Martin Weber, Leichlingen, all of (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 09/393,031

(22) Filed: Sep. 9, 1999

(30) Foreign Application Priority Data

Sep. 14, 1998  (EP) .................................................. 98117389

(51) Int. Cl.[7] .............................. C12P 19/34; C12N 15/00
(52) U.S. Cl. ........................................ 435/91.1; 435/320.1
(58) Field of Search .................................. 435/91.1, 320; 536/23.1, 25.4, 25.41; 514/44; 530/412

(56) References Cited

FOREIGN PATENT DOCUMENTS

WO 92/13963  8/1992 (WO).
WO 95/21250  8/1995 (WO).

OTHER PUBLICATIONS

Schorr, J. et al., "Plasmid DNA for Human Gene Therapy and DNA Vaccines," *Ann. N. Y. Acad. Sci.*, 772: 271–273 (1995).
Goldmark, P.J. and Linn, S., "Purification and Properties of the recBC DNase of *Escherichia coli* K–12", *J. Biol. Chem.*, 247: 1849–1860 (1972).
Murphy, K.C., "λ Gam Protein Inhibits the Helicase and χ–Stimulated Recombination Activites of *Escherichia coli* RecBCD Enzyme," *J. Bacteriol.*, 173: 5808–5821 (1991).
Isfort, R.J., "Enzymatic Purification of Plasmid DNA," *BioTechniques*, 12: 798–804 (1992).
Caplen et al., *Gene Therapy*, 1(2): 139–147 (1994).
Database WP1, Section Ch, Week 8516, Derwent Publications, Ltd., London, GB (1985).
Feliciello and Chinali, *Analytical Biochemistry*, 212: 394–401 (1993).
Holmes et al., *Analytical Biochemistry*, 114(1): 193–197 (1981).
Horn et al., *Humane Gene Therapy*, 6(5): 565–573 (1995).
Prazeres et al., *Journal of Chromatography*, 806(1): 31–45 (1998).
Sambrook et al., "Purification of Plasmid DNA by Precipitation with Polyethylene Glycol", *Plasmid Vectors*, 1.40–1.41, 1.46–1.47 (1985).
Sayers and Thompson, *Analytical Biochemistry*, 241: 186–189 (1996).
Sohail et al., *Pakistan Journal of Zoology*, 19(4): 407–412 (1987).
Sayers et al., "Identification and Eradication of a Denatured DNA Isolated during Alkaline Lysis–Based Plasmid Purification Procedures," 1996, Analytical Biochemistry, vol. 241, pp. 186–189.*
Jiang et al., "Nucleic acid immunization protects dogs against challenge with virulent canine parvovirus," Vaccine, Apr. 1998, vol. 16, No. 6, pp. 601–607.*
Palas et al., "Biochemical and Physical Characterization of Exonuclease V from *Escherichia coli*," The Journal of Biological Chemistry, 1990, vol. 265, No. 6, pp. 3447–3454.*
Isfort R J, "Enzymatic purification of plasmid DNA; e.g., plasmid MSVcL purification using RNA–ase–A, RNA–ase–T1, exonuclease, and ATP–dependent DNA–ase," Biotechniques, 1992, vol. 12, No. 6, pp. 798–804.*

* cited by examiner

*Primary Examiner*—John S. Brusca
*Assistant Examiner*—Young Kim
(74) *Attorney, Agent, or Firm*—Leon R. Yankwich; Thomas R. Berka

(57) ABSTRACT

The present invention relates to a method of producing covalently closed circular (ccc) DNA from a cultured cell or unicellular organism, preferably a bacterium, essentially free of genomic DNA. The method of the invention comprises the steps of precipitating a cleared lysate with an alcohol, washing and resuspension of the precipitate, digestion of the genomic DNA with a nuclease that cleaves linear DNA or circular DNA that includes a nick or a free 3' or 5' end but not ccc DNA, and finally, separation of the purified ccc DNA from the remainder of the product of the digestion step by contacting the product with an ion exchange material. ccc DNA obtained by the method, pharmaceutical compositions comprising the ccc DNA, and a kit for carrying out the method of the invention are also contemplated.

14 Claims, No Drawings

METHOD FOR PURIFYING COVALENTLY CLOSED CIRCULAR DNA

FIELD OF THE INVENTION

The present invention relates to the field of biotechnology and particularly to the field of DNA isolation and purification. The present invention involves a method for producing covalently closed circular DNA (ccc DNA) from a cell line or a unicellular organism, preferably a bacterium, essentially free of genomic DNA.

BACKGROUND OF THE INVENTION

The production of covalently closed circular DNA in pure form has become increasingly important in the past two decades. The development of DNA vaccines in the last few years has added to this demand. The purification protocol for ccc DNA requires its separation from the genomic DNA of the cultured cell or unicellular organism carrying the ccc DNA.

Standard protocols designed to simplify this process as far as possible have the problem that after the degradation step for genomic DNA the sample still comprises the degrading protein or fragments thereof. A partial answer to this problem is provided by such suppliers as Epicenter Technologies (Madison, Wisconsin, USA), which distributes an ATP-dependent DNAse under the tradename Plasmid-Safe™ for the separation of plasmid DNA (ccc DNA) from genomic DNA. The enzyme specifically cleaves linear DNA (such as genomic DNA) while leaving ccc DNA intact. The earliest identification of an enzyme of this class, namely of the ATP-dependent exonuclease RecBCD, was published in 1972 (Goldmark and Linn, *J. Biol. Chem.*, 247, 1849–1860).

In spite of such advances, proteinaceous impurities contained in the ccc DNA sample solutions generate problems when the ccc DNA is used for subcloning purposes. In addition, such impurities may cause adverse side effects when used in in vivo applications.

Thus, the technical problem underlying the present invention was to improve the existing protocols for separating ccc DNA from genomic DNA. In accordance with the present invention it was found that a novel process comprising a sequence of steps discussed in more detail below not only provides ccc DNA of a high purity grade but also removes proteinaceous impurities that could interfere with subsequent cloning steps or in vivo applications.

SUMMARY OF THE INVENTION

The method of the invention comprises the steps of precipitating a cleared lysate with an alcohol such as isopropanol and, after washing and resuspension of the precipitate, digesting the genomic DNA with a nuclease that cleaves linear DNA or circular DNA that includes a nick or comprises a free 3' end or 5' end but not ccc DNA. Finally, purified ccc DNA is separated from the remainder of the product of the digestion step by contacting said product with an ion exchange material. Preferably, the separation step is a chromatography step using an anion exchange resin, most preferably an anion exchange column. The invention also relates to purified ccc DNA obtained by the method of the invention, pharmaceutical compositions comprising said ccc DNA, and kits for carrying out the method of the invention.

Accordingly, the present invention relates to a method of producing covalently closed circular (ccc) DNA from a cell or unicellular organism wherein said ccc DNA is essentially free of genomic DNA comprising the steps of:

(a) precipitation of a cleared lysate of said cell or unicellular organism with 0.6–5 volumes of an alcohol;
(b) washing of the precipitate with an alcoholic solution;
(c) resuspension of the precipitate;
(d) digestion of the genomic DNA with a nuclease that cleaves linear DNA and/or circular DNA that comprises a nick or comprises a free 3' or 5' end but not ccc DNA; and
(e) separating purified ccc DNA from the remainder of the product of step (d) by contacting the product of step (d) with an ion exchange material, preferably an anion exchange material.

The present invention has the particular advantage that highly purified ccc DNA is obtained using an uncomplicated and comparatively inexpensive method. Yet, in spite of the method's simplicity, the critical sequence of steps can by no means be regarded as obvious. For example, when starting out to solve the aforementioned technical problems, attempts by the inventors to establish the step of employing a DNase directly after the lysis of bacteria by alkali treatment resulted in failure. This negative result is probably due to the presence of impurities, or salts, etc. in the lysate.

The method of the invention saves several hours of preparation time compared to the conventional procedures of adding the enzyme to a final stage of the DNA isolation process. Especially advantageous is the fact that with the current invention the use of toxic reagents like phenol or chloroform for the extraction of the remaining enzyme can be totally eliminated.

The ccc DNA obtained by the method of the invention can be used for a variety of purposes including cloning procedures and pharmaceutical applications such as vaccination. The ccc DNA may optionally be further purified, for example, by HPLC or may be prepared for storage, e.g., by lyophilization.

DEFINITIONS

The term "covalently closed circular DNA" as used herein refers to DNA molecules that have assumed a circular form in contrast to linear DNA molecules such as eukaryotic chromosomal DNA or bacterial chromosomal DNA that comprises a nick or comprises a free 3' or 5' end. Moreover, the circular structure of the above referenced DNA molecules is covalently closed. ccc DNA is well known in the art and is further described, for example, in K. G. Hardy (ed.), *Plasmid, a Practical Approach* (IRL Press Oxford U.K., Washington D.C., U.S.A., 1987).

The term "essentially free of genomic DNA" is intended to mean that more than 95% of the genomic DNA, preferably more than 98%, and most preferably more than 99% of the genomic DNA in a sample has been degraded and/or removed. Optimally, the ccc DNA isolated according to the invention is 100% purified or is as close to 100% purified as is within the limits of detection using standard assays.

The term "cleared lysate" is also well known in the art and refers to an aqueous solution containing plasmid DNA, RNA and proteins which is obtained after lysis of cultured cells or unicellular organisms and the separation of the cell debris, usually by filtration or centrifugation. For obtaining a cleared lysate, lysis of said cell or organism has to precede the steps recited above. Accordingly, in one embodiment, the method of the invention envisages an additional step that relates to the lysis of said cell or unicellular organism under conditions that leave the ccc DNA essentially intact. Methods for the lysis of cells and unicellular organisms are well know in the art and described, for example, in Sambrook et al., *Molecular Cloning, A Laboratory Handbook*, 2$^{nd}$ edition (CSH Press, Cold Spring Harbor, U.S.A. 1989).

DETAILED DESCRIPTION OF THE PREFERRED EMBODIMENTS

The present invention relates to a method for isolating covalently closed circular (ccc) DNA essentially free of genomic DNA from a cell or unicellular organism. ccc DNA obtained following the method of the invention is highly pure and homogenous, typically containing no detectable genomic DNA from the source cells or microorganisms.

The method according to the present invention for producing covalently closed circular (ccc) DNA from a cell or unicellular organism, wherein said ccc DNA is essentially free of genomic DNA, comprises the steps of:

(a) precipitation of a cleared lysate of said cell or unicellular organism with 0.6–5 volumes of an alcohol;

(b) washing of the precipitate with an alcoholic solution;

(c) resuspension of the precipitate;

(d) digestion of the genomic DNA with a nuclease that cleaves linear DNA and/or circular DNA that comprises a nick or comprises a free 3' or 5' end but not ccc DNA; and (e) separating purified ccc DNA from the remainder of the product of step (d) by contacting the product of step (d) with an ion exchange material, preferably an anion exchange material.

The method may be applied to the isolation of ccc DNA from any cell, whether prokaryotic or eukaryotic, harboring such DNA, including plasmid DNA, cosmid DNA or other DNA such as P1, BAC or PAC DNA. The method is particularly suitable for isolation of P1 DNA, which is a construct derived from a P1 phage, described, e.g., in Ausubel, *Current Protocols in Molecular Biology* (Green Publishing Associates and Wiley Interscience, N.Y. 1989), BAC (Bacterial Artificial Chromosome) DNA, or PAC (Phage Artificial Chromosome) DNA. The technical details and applications discussed herein for plasmids in many cases also apply to the above referenced DNAs, as is well known to the person skilled in the art. The method of the invention is particularly advantageous for the production of highly purified cosmid DNA, P1, BAC DNA or PAC DNA. This is due to the fact that cosmid DNA and the other DNA types referred to above are, as compared to "normal" plasmid DNA, present in a cell only in low copy numbers. Therefore, the percentage of genomic DNA in the overall amount of DNA is rather high. This high ratio is especially disadvantageous for a variety of applications, for example, the introduction of cosmid, P1, BAC or PAC DNA into in vitro cultured cells, and subcloning experiments will be accompanied by a high background of clones carrying genomic bacterial DNA inserts. Such disadvantages are eliminated according to the present invention, wherein genomic DNA can be substantially completely eliminated. Furthermore, the preparation of plasmids/cosmids or the other referenced DNAs according to GLP/GMP standards will be significantly simplified by incorporating the method of the invention into the preparation process.

The source of the ccc DNA may be any cell line or unicellular organism capable of harboring ccc DNA. A suitable unicellular organism may be a eukaryote, such as, especially, yeast or Aspergillus, or a prokaryote, including a bacterium or an archaebacterium. It is preferred in accordance with the present invention that said unicellular organism is a bacterium. In a particularly preferred embodiment, said bacterium is *E. coli*.

The precipitation step (a) is applied to a cleared lysate, which may be obtained by treating a sample of cultured cells or organisms by any suitable method known in the art. Such methods will include, e.g., alkaline lysis, detergent lysis, RNAse treatment, lysozyme/EDTA, and the like, and will avoid procedures, such as vortexing, sonication or freeze/thaw that might damage or shear the target ccc DNA.

The precipitation step of the method separates the DNA of the cells from other components, including some RNA and proteins in the cleared lysate. Precipitation is effected by addition of an alcohol within a certain range of volumes of alcohol added which is between 0.6 and 5 volumes, preferably 0.6 to 3 volumes. Examples of preferred alcohols are isopropanol and ethanol. Preferably, the quantum of isopropanol employed is about 0.6–1.0 times the volume of the lysate or a solution comprising said lysate and more preferably is about 0.6 times said volume. Ethanol is preferably added in an amount of about 2.0–3.0 volumes and more preferably in an amount of 2.5 volumes. Other alcohols, such as methanol, butanols, pentanols and the like may also be used, however these are less preferred because of such factors as less efficient or complete precipitation of DNA, less enrichment of the sample with respect to RNA or protein impurities, or toxicity that may be undesirable considering the ultimate application intended for the purified ccc DNA product.

The subsequent washing step (b) is preferably carried out with a solution of ethanol in water which is most preferably a 70% ethanol solution. The washing step can be repeated one or more times. Subsequent to the washing step(s) it may be advantageous to at least partially dry the precipitate. This can be done by a variety of methods well known in the art.

In accordance with the present invention, it is additionally preferred that said resuspension in step (c) is carried out in a reaction buffer suitable for use with a high activity nuclease. Specific examples of such reaction buffers are set forth in the examples to follow. However, the buffer conditions supporting a high activity can be adjusted by the person skilled in the art on the basis of common technical knowledge and the teachings of this invention without further experimentation. In one especially preferred embodiment, the nuclease is added to the reaction buffer directly before resuspension. In another most preferred embodiment, the nuclease is added after the precipitate has been resuspended. Other embodiments in this regard, that the person skilled in the art might envisage, e.g., addition during resuspension, are likewise covered by the invention. Of course, the above embodiments also comprise adding a concentrate of the buffers in combination with a diluent, for example, deionized water.

The resuspended DNA is subjected to digestion (step (d)) using a nuclease that leaves ccc DNA intact but degrades linear DNA or DNA having a nick or a free 3' or 5' end. The nuclease employed in the digestion step of the invention may be an endonuclease or an exonuclease. In a preferred embodiment of the method of the invention, said nuclease that cleaves linear DNA, circular DNA that comprises a nick or comprises a free 3' or 5' end but not ccc DNA is an ATP-dependent exonuclease. Most preferably, said ATP-dependent exonuclease is the exonuclease RecBCD (EC 3.1.11.5).

A particular advantage of this type of enzyme is the dependency of its activity on ATP. Consequently, the practitioner has a distinct means in his hands to trigger, direct or stop the degradation of the genomic DNA.

The final separation step (e) is carried out by contacting the digest of step (d) with an ion exchange material, preferably an anion exchange material. It is furthermore preferred in accordance with the present invention that said separation in step (e) is effected by chromatography, e.g., by running said product of step (d) over an anion exchange column and recovering purified ccc DNA in the eluate.

This embodiment is particularly advantageous since large batches of product can be purified to a high degree of purity using a convenient procedure that may be automated. The column will retain impurities such as nuclease or fragments thereof as well as other proteinaceous material that may have remained in the sample from the precipitation step. The eluted material comprises the highly purified ccc plasmid DNA which may be further processed, for example, bottled, freeze-dried, precipitated, etc., according to conventional protocols.

Preferred anion exchange materials are based on a polymeric inorganic support material, such as acryl resin, dextran agarose, or a combination thereof, wherein preferably the groups bound to the anion exchanger have a surface charge from 1 to 4 $\mu$M/ml of support surface area, corresponding to the 0.5 to 500 pM/ml. The chromatographic support material described in International patent publication WO 95/21177 may be preferably used as a modified porous or non-porous inorganic and/or organic material. Further anion exchange materials, such as QIAGEN DEAE Sepharose, Q Sepharose (Pharmacia), DEAE Sephadex (Pharmacia), Phoros 20 M/P or Phoros 50 M/P or Hyper D may also be used.

As is well known in the art, there are different forms of ccc DNA. In accordance with the present invention, it is preferred that said ccc DNA is in the form of a plasmid. As is also well known, plasmids are often used as vectors. Thus, the method of the invention will be particularly advantageous for producing highly purified plasmids and in particular for obtaining plasmids with low copy numbers.

Plasmid vectors that may be advantageously purified using the invention may be expression vectors and/or gene transfer or targeting vectors. Expression vectors derived from viruses such as retroviruses, vaccinia virus, adeno-associated virus, herpes viruses, or bovine papilloma virus, may be used for delivery of the vector into targeted cell populations. Methods that are well known to those skilled in the art can be used to construct recombinant viral vectors; see, for example, the techniques described in Sambrook et al., loc. cit. and Ausubel, *Current Protocols in Molecular Biology* (Green Publishing Associates and Wiley Interscience, N.Y. 1989). Alternatively, the vectors can be reconstituted into liposomes for delivery to target cells. The vectors can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook et al., loc. cit.

Such vectors may further include genes such as marker genes which allow for the selection of said vector in a suitable host cell and under suitable conditions. Preferably, the vector comprises polynucleotide sequences which are operatively linked to expression control sequences allowing expression in prokaryotic or eukaryotic host cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in prokaryotic host cells include, e.g., the PL, lac, trp or tac promoter in *E. coli;* and examples for regulatory elements permitting expression in eukaryotic host cells include the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells. Beside elements which are responsible for the initiation of transcription, such regulatory elements may also comprise transcription termination signals, such as the SV40-poly-A site or the tk-poly-A site, downstream of the polynucleotide. Furthermore, depending on the expression system used, leader sequences capable of directing the polypeptide to a cellular compartment or secreting it into the extracellular medium may be added to the coding sequence of a polynucleotide isolated in accordance with the invention. Such sequences are well known in the art. The leader sequence(s) is (are) typically assembled in appropriate phase with translation, initiation and termination sequences, and, preferably, a leader sequence capable of directing secretion of translated protein, or a portion thereof, into the periplasmic space or extracellular medium is employed. Optionally, the heterologous sequence for expression can encode a fusion protein including an C- or N-terminal identification peptide imparting desired characteristics, e.g., stabilization or simplified purification of the expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL).

Preferably, the expression control sequences will be eukaryotic promoter systems in vectors capable of transforming or transfecting eukaryotic host cells, but control sequences for prokaryotic hosts may also be used.

As mentioned above, the vector isolated in accordance with the present invention may also be a gene transfer or targeting vector. Gene therapy, which is based on introducing therapeutic genes into cells by ex vivo or in vivo techniques is one of the most important applications of gene transfer. Suitable vectors and methods for in vitro or in vivo gene therapy are described in the literature and are known to the person skilled in the art. See, e.g., Giordano, *Nature Medicine,* 2, 534–539 (1996); Schaper, *Circ. Res.,* 79, 911–919 (1996); Anderson, *Science,* 256, 808–813 (1992); Isner, *Lancet,* 348, 370–374 (1996); Muhlhauser, *Circ. Res.,* 77,1077–1086 (1995); Wang, *Nature Medicine,* 2, 714–716 (1996); WO 94/29469; WO 97/00957 or Schaper, *Current Opinion in Biotechnology,* 7, 635–640 (1996), and references cited therein. The polynucleotides and vectors prepared using the method of the invention may be designed for direct introduction or for introduction via liposomes or viral vectors (e.g., adenoviral, retroviral) into the cell. Preferably, said cell is a germ line cell, embryonic cell, or egg cell or derived therefrom, most preferably said cell is a stem cell.

A variety of uses for the ccc DNA of the invention have been indicated hereinabove. Particularly preferred are uses in molecular diagnostics.

A particularly important use of said ccc DNA is in therapeutic applications. Consequently, the invention also relates to a composition, preferably a pharmaceutical composition, comprising the purified ccc DNA of the invention and optionally a pharmaceutically acceptable carrier and/or diluent.

As has been pointed out hereinabove, in vivo applications, especially with humans, require a high purity grade for the administered material. The method of the invention provides for such a high purity grade or at least provides for a material that needs only one further step of processing (e.g., final purification or concentration, for example, by HPLC) in order to have the required purity grade for such special applications. ccc DNA obtained using the method of the present invention is advantageously employed in such applications calling for high purity material, because the method of the invention does not employ toxic materials.

The pharmaceutical compositions of the present invention may include a pharmaceutically acceptable carrier and/or diluent. Suitable pharmaceutical carriers are well known in the art and include phosphate buffered saline solutions, water, emulsions such as oil/water emulsions, various types of wetting agents, sterile solutions, etc. Compositions comprising such carriers can be formulated by well known conventional methods. These pharmaceutical compositions can be administered to the subject at a suitable dose. Administration of suitable compositions may be effected in a variety of ways as appropriate, e.g., by intravenous, intraperitoneal, subcutaneous, intramuscular, topical, intradermal, intranasal or intrabronchial administration. The dosage and dosage regimen for such compositions will be determined by practitioner physician based on clinical factors. As is well known in the medical arts, appropriate dosages for any one patient depend upon many factors, including the patient's size, body weight, age, the particular compound to be administered, sex, time and route of administration, general health, and other drugs being administered concurrently. A typical dose can be, for example, in the range of 0.001 to 1000 $\mu$g (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 $\mu$g to 10 mg units per day. If the regimen is a continuous infusion, it should also be in the range of 1 $\mu$g to 10 mg units per kilogram of body weight, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases (propellants), and the like. Furthermore, the pharmaceutical composition of the invention may comprise additional active ingredients such as interleukins or interferons depending on the intended use of the pharmaceutical composition.

In a preferred embodiment of the invention, said pharmaceutical composition is a vaccine. As to the amount of ccc DNA present in a vaccine as well as its mode of delivery, reference is made to the description above with respect to pharmaceutical compositions. In general, DNA vaccines will be comprised of said ccc DNA, typically in a dose of $10^6$ to $10^{12}$ ccc DNA molecules.

Performing the ccc DNA isolation method described herein will be facilitated using a kit comprising:

(a) an ATP-dependent exonuclease;

(b) an exonuclease buffer; and (c) an adjustment buffer;

and optionally any of (d) a lysis buffer;

(e) a resuspension buffer;

(f) a neutralization buffer;

(g) an equilibration buffer;

(h) a reaction buffer;

(i) a wash buffer;

(j) an elution buffer; and (k) TE buffer (Tris/EDTA buffer).

The components of the kit of the invention may be packaged in containers such as vials, optionally in buffers and/or solutions. The components of the kit will also advantageously be accompanied by instructions for their use in accordance with the ccc DNA isolation method as described herein. If appropriate, one or more of said components may be packaged in one and the same container.

The exonuclease component is conveniently provided in a lyophilized form. The adjustment buffer serves the purpose of adjusting the salt concentration prior to applying the resuspended and digested sample to the ion exchange material.

In a preferred embodiment of the kit according to the invention, said ATP-dependent exonuclease is the exonuclease RecBCD.

The method of the invention is further illustrated by the examples that follow. The examples are provided by way of illustration and are not intended in any way to limit the scope of the invention.

EXAMPLE 1

Preparation of BAC/PAC/P1/Cosmid DNA

This protocol is for preparation of up to 50 $\mu$g of BAC, PAC, P1 or up to 200 $\mu$g of cosmid DNA using a QIAGEN-tip® 500 (Plasmid Maxi Kit) anion exchange column.

Materials:

BAC/PAC/P1/Cosmid Maxi Kit (5)

| | |
|---|---|
| QIAGEN-tip 500 | 5 |
| Buffer P1 | 110 ml |
| Buffer P2 | 110 ml |
| Buffer P3 | 110 ml |
| Buffer QBT | 60 ml |
| Buffer QC | 2 × 205 ml |
| Buffer QF | 110 ml |
| RNase A | 11 mg (100 mg/ml) |
| ATP-dependent Exonuclease | 5 × 115 $\mu$g |
| ATP solution (100 mM) | 1.75 ml |
| Reaction Buffer | 60 ml |
| Buffer QS (Adjustment Buffer) | 60 ml |
| Exonuclease Buffer | 1.5 ml |
| Folded filters | 5 |
| Protocol | 1 |

Composition of buffers:

| Buffer | Composition | Storage |
|---|---|---|
| Buffer P1 (Resuspension Buffer) | 50 mM Tris-HCl, pH 8.0; 10 mM EDTA; 100 µg/ml RNase A | 4° C., after addition on RNase A |
| Buffer P2 (Lysis Buffer) | 200 mM NaOH, 1% SDS | room temp. |
| Buffer P3 (Neutralization Buffer) | 3.0 M potassium acetate | room temp. or 4° C. |
| Buffer QBT (Equilibration Buffer) | 750 mM NaCl; 50 mM MOPS, pH 7.0; 15% isopropanol; 0.15% Triton® X-100 | room temp. |
| Buffer QC (Wash Buffer) | 1.0 M NaCl; 50 mM MOPS, pH 7.0; 15% isopropanol | room temp. |
| Buffer QF (Elution Buffer) | 1.25 M NaCl; 50 mM Tris, pH 8.5; 15% isopropanol | room temp. |
| Buffer QS (Adjustment Buffer) | 1.5 M NaCl; 100 mM MOPS, pH 7.0; 15% isopropanol | room temp. |
| Exonuclease Buffer | 20 mM KCl; 20 mM potassium-phosphate, pH 7.5 | room temp. |
| Reaction Buffer | 50 mM Tris-HCl; 10 mM $MgCl_2$, pH 8.5 | room temp. |
| TE (Tris/EDTA) | 10 mM NaCl; 10 mM Tris-HCl, pH 8.0; 1 mM EDTA | room temp. |

Recommended culture volumes:

|  | QIAGENA-tip® 500 |
|---|---|
| BAC | 500 ml |
| PAC | 500 ml |
| P1 | 500 ml |
| Cosmid | 500 ml |

The following steps were taken before starting the actual separations:
(a) Added RNase A solution to Buffer P1 before use. Used one vial of RNase A (spun down briefly before use) per bottle of Buffer P1, to give a final concentration of 100 µg/ml.
(b) Used one vial of ATP-dependent exonuclease per preparation. Immediately before use, the exonuclease of each vial was resuspended in 225 µl of Exonuclease Buffer.
c) Checked Buffer P2 for SDS precipitation due to low storage temperatures. If necessary, SDS was dissolved by warming to 37° C.
d) Pre-chilled Buffer P3 to 4° C.

Procedure

1. A single colony was picked from a freshly streaked selective plate and a starter culture of 2–5 ml LB-Miller medium containing the appropriate selective antibiotic inoculated. It was then incubated for ~8 hours at 37° C. with vigorous shaking (~300 rpm). A flask with a volume of at least 4 times the volume of the culture was used.

2. The starter culture was diluted 1/500 to 1/1000 into 500 ml selective LB-Miller medium. It was then grown at 37° C. for 12–16 hours with vigorous shaking (~300 rpm). A flask or vessel with a volume of at least 4 times the volume of the culture was used. The culture should reach a cell density of approximately $1 \times 10^9$ cells per ml.

3. The bacterial cells were harvested by centrifugation at 6000×g for 15 min. at 4° C. 6000×g corresponds to 6000 rpm in Sorvall® GSA or GS3 or Beckman® JA-10 rotors. All traces of supernatant were removed by inverting the open centrifuge tube until all medium had been drained.

4. The bacterial pellet was resuspended in 20 ml of Buffer P1. Care was taken that RNase A is added to Buffer P1. The bacteria were resuspended completely leaving no cell clumps. Optionally, the resuspended bacteria can be split into 2×10 ml. Then both samples are processed through steps 5 and 6, and the samples recombined after step 7, before the filtration.

5. 20 ml of Buffer P2 were added, mixed gently but thoroughly by inverting 4–6 times, and incubated at room temperature for 5 min. Vortexing is avoided, as this will result in shearing of the BAC, PAC, P1 or cosmid DNA. The lysate should appear viscous. The lysis reaction is not allowed to proceed for more than 5 min. After use, the bottle containing Buffer P2 was closed immediately to avoid acidification of Buffer P2 from $CO_2$ in the air.

6. 20 ml of chilled Buffer P3 were added, mixed immediately but gently by inverting 4–6 times, and incubated on ice for 10 min. Precipitation was enhanced by using chilled Buffer P3 and incubation on ice. After addition of Buffer P3, a cloudy and very viscous precipitate containing genomic DNA, proteins, cell debris, and SDS became visible. Thorough mixing avoids localized potassium dodecyl sulfate precipitation.

7. Centrifugation was carried out at ≧20,000×g for 30 min. at 4° C. The supernatant containing BAC/PAC/P1/Cosmid DNA was removed promptly. Before loading the centrifuge, the sample was mixed again. Centrifugation was performed in non-glass tubes (e.g., polypropylene). A centrifugal force of 20,000×g corresponds to 12,000 rpm in a Beckman® JA-17 rotor or 13,000 rpm in a Sorvall® SS-34 rotor. After centrifugation, the supernatant was and should be clear. If two samples have been processed in parallel since step 4, they should be recombined now for step 8.

8. The cleared lysate was filtered through a distilled water-prewetted folded filter. This filtration step is carried out to avoid precipitation of suspended or particulate material in step 9, which could lead to suboptimal exonuclease performance in step 12.

9. The DNA was precipitated by adding 35 ml (0.6 volumes) room-temperature isopropanol to the cleared lysate. It was then mixed and centrifuged immediately at ≧15,000×g for 30 min. at 4° C. The supernatant was then carefully decanted. The isopropanol should be at room temperature in order to minimize salt precipitation, although centrifugation was carried out at 4° C. to prevent overheating of the sample. A centrifugal force of 15,000×g corresponds to 9,500 rpm in a Beckman® JS-13 rotor and 11,000 rpm in a Sorvall® SS-34 rotor. This isopropanol pellet contains proteins and genomic DNA and is therefore typically easy to see.

Optionally, the cleared lysate can alternatively be split into 2×50 ml tubes and centrifuged at 5000×g for 60 minutes in, e.g., a Heraeus Minifuge. Both samples should be continued to be processed through step 10 and the samples recombined in step 11, before exonuclease digestion.

10. The DNA pellet was washed with 5 ml of room-temperature 70% ethanol, and centrifuged at >15,000×g for 15 min. The supernatant was decanted carefully, without disturbing the pellet. The 70% ethanol removes precipitated salt and replaces isopropanol with the more volatile ethanol, making the DNA easier to redissolve.

11. The tube containing the DNA pellet was placed upside down on a paper towel and the DNA was allowed to air-dry for 2–3 min. Any additional liquid that may have been visible on the tube opening was carefully removed, then the DNA was carefully redissolved in 9.5 ml of Reaction Buffer, until the DNA was completely dissolved. Dissolving the DNA should only take place by very gentle shaking. If two samples have been processed in parallel since step 9, they should be reunified now for step 12.

12. 200 µl of an ATP-dependent exonuclease (previously dissolved in Exonuclease Buffer) and 300 µl ATP Solution (100 mM ATP solution) were added to the dissolved DNA, mixed gently but thoroughly, and incubated in a water bath or heating block at 37° C. for 60 minutes. During this step genomic DNA and nicked BAC/PAC/P1/Cosmid DNA will be digested by the exonuclease. Only supercoiled DNA will remain for further purification.

13. A QIAGEN-tip® 500 was equilibrated by applying 10 ml Buffer QBT and allowing the column to empty by gravity flow. Flow of buffer will begin automatically by reduction in surface tension due to the presence of detergent in the equilibration buffer. The QIAGEN-tip was allowed to drain completely. QIAGEN-tips can be left unattended, since the flow of buffer will stop when the meniscus reaches the upper frit in the column.

14. 10 ml of QS Buffer was added to the DNA sample from step 12, the whole sample applied to the QIAGEN-tip and allowed to enter the resin by gravity flow.

15. The QIAGEN-tip was washed with 2×30 ml Buffer QC.

16. The DNA was eluted with 15 ml Buffer QF, prewarmed to 65° C. Use of prewarmed buffer QF will enhance efficient elution of large DNA molecules. The eluate was collected in a 30 ml tube. Use of polycarbonate centrifuge tubes is not recommended as polycarbonate is not resistant to the alcohol used in subsequent steps.

17. DNA was precipitated by adding 10.5 ml (0.7 volumes) room-temperature isopropanol to the eluted DNA, then mixed and centrifuged immediately at ≧15,000×g for 30 min. at 4° C. The supernatant was carefully decanted. All solutions were and should be at room temperature in order to minimize salt precipitation, although centrifugation is carried out at 4° C. to prevent overheating of the sample. A centrifugal force of 15,000×g corresponds to 9,500 rpm in a Beckman® JS-13 rotor and 11,000 rpm in a Sorvall® SS-34 rotor. Isopropanol pellets have a glassy appearance and may be more difficult to see than the fluffy, salt-containing pellets that result from ethanol precipitation. Marking the outside of the tube before centrifugation allows the pellet to be more easily located. Isopropanol pellets are also more loosely attached to the side of the tube, and care should be taken when removing the supernatant.

18. The DNA pellet was washed with 5 ml of room-temperature 70% ethanol, and centrifuged at >15,000×g for 15 min. The supernatant was carefully decanted without disturbing the pellet. The 70% ethanol removes precipitated salt and replaces isopropanol with the more volatile ethanol, making the DNA easier to redissolve.

19. The pellet was air-dried for 5–10 min., and the DNA redissolved in a suitable volume of buffer (e.g., TE, pH 8.0, or 10 mM Tris, pH 8.5). The DNA pellet was redissolved by rinsing the walls to recover all the DNA, especially if glass tubes have been used. Pipetting the DNA up and down to promote resuspension may cause shearing and should be avoided. Overdrying the pellet will make the DNA difficult to redissolve. The DNA may also be difficult to dissolve if it is too acidic. DNA dissolves best under slightly alkaline conditions.

EXAMPLE 2

Preparation of about 100 ma Genomic free Plasmid DNA 66 g biomass of *E. coli* bacteria containing the plasmid pCMVS2.S (Whalen et al., *Proc. Natl. Acad. Sci. USA*, 92, 5307–5311(1995) was lysed with 1 L each of buffers P1, P2 and P3 according to EP-A-743 949.

After lysis the cell debris were removed as described in EP-A-781 291 or by centrifugation at 20,000×g.

The plasmid DNA was precipitated by adding 0.6 vol. (2.25 l) of isopropanol and centrifuged at 20,000×g for 30 min. The pellet was redissolved in 100 ml of reaction buffer (see Example 1). 30 ml ATP solution (100 mM ATP) and 10 mg of RecBCD enzyme redissolved in 20 ml of exonuclease buffer (20 mM KCl, 20 mM potassium phosphate, pH 7.5) was added to the solution and incubated for 120 min. at 37° C. The solution was diluted with 150 ml of buffer QS and loaded onto a QIAGEN® Ultrapure 100 anion exchange column (QIAGEN GmbH, Hilden, DE), which had been equilibrated with 750 mM NaCI and processed following the Ultrapure 100 protocol provided by the manufacturer.

The above procedures resulted in a DNA product which has less than 1% genomic DNA and consists of 99% supercoil (ccc DNA) molecules. The anion exchange purification removes the RecBCD enzyme with a 99% efficacy. This DNA fulfills the QC standards for use in clinical applications of gene therapy and DNA vaccination. The actual amount of ccc DNA obtained may vary, for example depending on the plasmid isolated.

The subject matter of the patents and other publications listed above is incorporated herein by reference.

What is claimed is:

1. A method of isolating covalently closed circular (ccc) DNA from a cell or unicellular organism wherein said isolated ccc DNA is essentially free of genomic DNA comprising the steps of:
   (a) precipitation of a cleared lysate of said cell or unicellular organism with 0.6 to 5 volumes of an alcohol;
   (b) washing the precipitate with an alcohol solution;
   (c) resuspension of the precipitate;
   (d) digestion of the resuspended precipitate with a RecBCD nuclease (EC 3.1.11.5); and
   (e) separating purified ccc DNA from the remainder of the product of step (d) by contacting the product of step (d) with an ion exchange material.

2. The method of claim 1, wherein said ccc DNA is plasmid DNA.

3. The method of claim 1, wherein said ccc DNA is cosmid DNA, P1 DNA, BAC DNA or PAC DNA.

4. The method of claim 1, wherein said unicellular organism is a bacterium.

5. The method of claim 4, wherein said bacterium is *E. coli*.

6. The method of claim 1, wherein precipitation in step (a) is effected using isopropanol or ethanol.

7. The method of claim 1, wherein said alcohol solution in step (b) is a solution of ethanol in water.

8. The method of claim 7, wherein said ethanol solution is a 70% ethanol solution.

9. The method of claim 1, wherein said resuspension in step (c) is carried out in a reaction buffer suitable for maintaining high activity of said nuclease.

10. The method of claim 9, wherein said resuspension step (c) is carried out using a reaction buffer that includes the nuclease.

11. The method claim 9, wherein the nuclease is added to said resuspension product of step (c).

12. The method of claim 1, wherein said separation in step (e) is effected by applying the product of step (d) to an anion exchange chromatography column and recovering said purified ccc DNA in the eluate.

13. The method of claim 12, wherein said anion exchange material is selected from the group of acryl resins, dextran agaroses or combinations thereof, wherein the groups bound to the anion exchanger have a surface charge from 1 to 4 μM/ml of support surface area, corresponding to the 0.5 to 500 μM/ml.

14. A kit comprising:
   (a) a RecBCD nuclease;
   (b) an exonuclease buffer; and (c) an adjustment buffer;
and optionally any of
  (d) a lysis buffer;
  (e) a resuspension buffer;
  (f) a neutralization buffer;
  (g) an equilibration buffer;
  (h) a reaction buffer;
  (i) a wash buffer;
  (j) an elution buffer;
  (k) TE. and
wherein said kit further comprises instructions for use of the components of the kit in a method for the isolation of ccc DNA essentially free of genomic DNA according to claim 1.

* * * * *